(12) United States Patent
Remmereit

(10) Patent No.: US 11,813,271 B2
(45) Date of Patent: Nov. 14, 2023

(54) SIALIC ACID COMPOSITIONS FOR THE USE OF INHIBITING AND TREATING CORONAVIRUS INFECTION

(71) Applicant: LifeScience AS, Orsta (NO)

(72) Inventor: Jan Remmereit, Hovdebygda (NO)

(73) Assignee: LifeScience AS, Orsta (NO)

( * ) Notice: Subject to any disclaimer, the term of this patent is extended or adjusted under 35 U.S.C. 154(b) by 0 days.

(21) Appl. No.: 17/916,104

(22) PCT Filed: Mar. 31, 2021

(86) PCT No.: PCT/IB2021/000200
§ 371 (c)(1),
(2) Date: Sep. 30, 2022

(87) PCT Pub. No.: WO2021/198774
PCT Pub. Date: Oct. 7, 2021

(65) Prior Publication Data
US 2023/0128687 A1    Apr. 27, 2023

Related U.S. Application Data

(60) Provisional application No. 63/003,477, filed on Apr. 1, 2020.

(51) Int. Cl.
*A61K 31/7012* (2006.01)
*A61P 31/14* (2006.01)

(52) U.S. Cl.
CPC .......... *A61K 31/7012* (2013.01); *A61P 31/14* (2018.01)

(58) Field of Classification Search
None
See application file for complete search history.

(56) References Cited

U.S. PATENT DOCUMENTS 9,522,158 B2 *  12/2016  Remmereit ............. A61P 31/14

FOREIGN PATENT DOCUMENTS

| CN | 111481560 | 8/2020 |
| CN | 112472691 | 3/2021 |
| WO | 2019/073298 | 4/2019 |

OTHER PUBLICATIONS

Hou, Pengbo, et al. "Exogenous supplement of N-acetylneuraminic acid improves macrophage reverse cholesterol transport in apolipoprotein E-deficient mice." Lipids in Health and Disease 18.1 (2019): 1-6.*
International Search Report & Written Opinion, International Patent Application No. PCT/IB2021/000200, dated Sep. 16, 2021, 15 pages.
Yang Yang et al. "Traditional Chinese Medicine in the Treatment of Patients Infected with 2019-New Coronavirus (SARS-CoV-2): A Review and Perspective" International Journal of Biological Sciences, vol. 16, No. 10, Jan. 1, 2020, pp. 1708-1717.

* cited by examiner

*Primary Examiner* — Patrick T Lewis
(74) *Attorney, Agent, or Firm* — CASIMIR JONES S.C.; J. Mitchell Jones

(57) ABSTRACT

The present invention relates to the use of compositions comprising sialic acid to inhibit or treat coronavirus infections, and in particular those caused by SARS-CoV-2 (Severe Acute Respiratory Syndrome Coronavirus 2).

38 Claims, 2 Drawing Sheets

Neu5Ac   Neu5Gc

Neu5Ac   Neu5Gc

SIALIC ACID COMPOSITIONS FOR THE USE OF INHIBITING AND TREATING CORONAVIRUS INFECTION

CROSS REFERENCE TO RELATED APPLICATIONS

This application claims the benefit of U.S. Prov. Appl. 63/003,477 filed Apr. 1, 2020, the entire contents of which are incorporated herein by reference.

FIELD OF THE INVENTION

The present invention relates to the use of compositions comprising sialic acid to inhibit or treat coronavirus infections, and in particular those caused by SARS-CoV-2 (Severe Acute Respiratory Syndrome Coronavirus 2).

BACKGROUND OF THE INVENTION

Coronaviruses are a family of viruses that can cause illnesses such as the common cold, severe acute respiratory syndrome (SARS) and Middle East respiratory syndrome (MERS). In 2019, a new coronavirus was identified as the cause of a disease outbreak that originated in China. The virus is now known as the severe acute respiratory syndrome coronavirus 2 (SARS-CoV-2). The disease it causes is called coronavirus disease 2019 (COVID-19). Cases of COVID-19 have been reported around the world and WHO declared a global pandemic in March 2020.

Signs and symptoms of COVID-19 may appear two to 14 days after exposure and can include: fever; cough; and shortness of breath or difficulty breathing. Other symptoms can include: tiredness; aches; runny nose; and sore throat. The severity of COVID-19 symptoms can range from very mild to severe. Some people have no symptoms. People who are older or have existing chronic medical conditions, such as heart or lung disease or diabetes, may be at higher risk of serious illness.

What is needed in the art are safe compositions for inhibiting or treating infection by SARS-CoV-2.

SUMMARY OF THE INVENTION

The present invention relates to the use of compositions comprising sialic acid to inhibit or treat coronavirus infections, and in particular those caused by SARS-CoV-2 (Severe Acute Respiratory Syndrome Coronavirus 2).

Accordingly, in some preferred embodiments, the present invention provides methods for treating or inhibiting infection by SARS-CoV-2 (Severe Acute Respiratory Syndrome Coronavirus 2), in a human or animal subject, the method comprising: administering a composition comprising sialic acid in an effective concentration to the subject under conditions such that infection by SARS-CoV-2 is inhibited or treated.

In some preferred embodiments, the present invention provides methods for prophylaxis of infection by SARS-CoV-2 (Severe Acute Respiratory Syndrome Coronavirus 2), in a human or animal subject, the method comprising: administering a composition comprising sialic acid in an effective concentration to the subject under conditions such that infection by SARS-CoV-2 is inhibited.

In some preferred embodiments, the present invention provides sialic acid for use in treating or inhibiting infection by SARS-CoV-2 (Severe Acute Respiratory Syndrome Coronavirus 2) in a human or animal subject.

In some preferred embodiments, the present invention provides sialic acid for use in prophylaxis of SARS-CoV-2 (Severe Acute Respiratory Syndrome Coronavirus 2) infection in a human or animal subject.

In some preferred embodiments, the sialic acid is elected from the group consisting of n-acetylneuraminic acid (NANA) and n-glycolylneuraminic acid (NGNA). In some preferred embodiments, the sialic acid is NANA.

In some preferred embodiments, the sialic acid is administered intranasally. In some preferred embodiments, the effective concentration of sialic acid is from about 0.1 to about 100 mg/ml in an aqueous solution. In some preferred embodiments, effective concentration of sialic is from about 0.5 to about 50 mg/ml in an aqueous solution. In some preferred embodiments, the daily dosage of sialic acid is from about 0.1 to 100 mg sialic acid/nostril/day. In some preferred embodiments, the daily dosage of sialic acid is from about 0.1 to 10 mg sialic acid/nostril/day. In some preferred embodiments, the pH of composition comprising sialic acid, preferably in aqueous solution, is from 2.0 to 4.0. In some preferred embodiments, the pH of composition comprising sialic acid, preferably in aqueous solution, is from 2.5 to 3.7. In some preferred embodiments, the pH of composition comprising sialic acid, preferably in aqueous solution, is from 2.8 to 3.2. In some preferred embodiments, the daily dosage of sialic acid is delivered in from 2 to 8 administrations per day. In some preferred embodiments, the composition further comprises a thixotropic agent.

In some preferred embodiments, the sialic acid is administered orally. In some preferred embodiments, the daily dosage of sialic acid is from 20 to 200 grams. In some preferred embodiments, the daily dosage of sialic acid is from 50 to 150 grams. In some preferred embodiments, the daily dosage is administered in from 1 to 20 doses. In some preferred embodiments, the sialic acid is administered as a aqueous solution. In some preferred embodiments, the aqueous solution comprising an additional agent selected from the group consisting of a flavoring agent, a stabilization agent and a preservative agent, wherein the additional agent does not naturally occur with sialic acid.

In some preferred embodiments, the subject is at risk for infection by SARS-CoV-2.

In some preferred embodiments, the subject has COVID-19.

Additional embodiments are described herein.

Definitions

As used herein, the term "SARS-CoV-2 (severe acute respiratory syndrome coronavirus 2)" includes any strain of coronavirus identified as being SARS-CoV-2 including mutants of SARS-CoV-2 reference genomic sequences.

As used herein, the term "inhibits" when used in reference to infection by SARS-CoV-2 refers to a reduction in infection in subjects exposed to SARS-CoV-2.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Administering" or "administration of" a substance, a compound or an agent to a subject can be carried out using one of a variety of methods known to those skilled in the art. For example, sialic acid can be administered, intravenously, arterially, intradermally, intra-muscularly, intraperitonealy, intravenously, subcutaneously, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

A "therapeutically effective amount" or a "therapeutically effective dose" of a drug or agent, such as sialic acid, is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of symptoms of the condition being treated, such as COVID-19. The skilled worker can readily determine the effective amount for a given situation by routine experimentation.

A "prophylactically effective amount" or a "prophylactically effective dose" of a drug or agent, such as sialic acid, is an amount of a drug or an agent that, when administered to a subject will have the intended prophylactic effect. The full prophylactic effect does not necessarily occur by administration of one dose, and may occur only after administration of a series of doses. Thus, a prophylactically effective amount may be administered in one or more administrations. The precise effective amount needed for a subject will depend upon, for example, the subject's size, health and age, the nature and extent of symptoms of the condition being treated, such as SARS-CoV-2 infection. The skilled worker can readily determine the effective amount for a given situation by routine experimentation. "Treating" a condition or patient refers to taking steps to obtain beneficial or desired results, including clinical results. Beneficial or desired clinical results include, but are not limited to, alleviation, amelioration, or slowing the progression, of one or more symptoms associated with COVID-19. In certain embodiments, treatment may be prophylactic, such as for the prevention of infection by SARS-CoV-2.

As used herein, the term "dietary supplement" refers to a small amount of a compound for supplementation of a human or animal diet packaged in single or multiple does units. Dietary supplements do not generally provide significant amounts of calories but may contain other micronutrients (e.g., vitamins or minerals).

As used herein, the term "nutritional supplement" refers to a composition comprising a "dietary supplement" in combination with a source of calories. In some embodiments, nutritional supplements are meal replacements or supplements (e.g., nutrient or energy bars or nutrient beverages or concentrates).

DETAILED DESCRIPTION OF THE INVENTION

Figure 1:
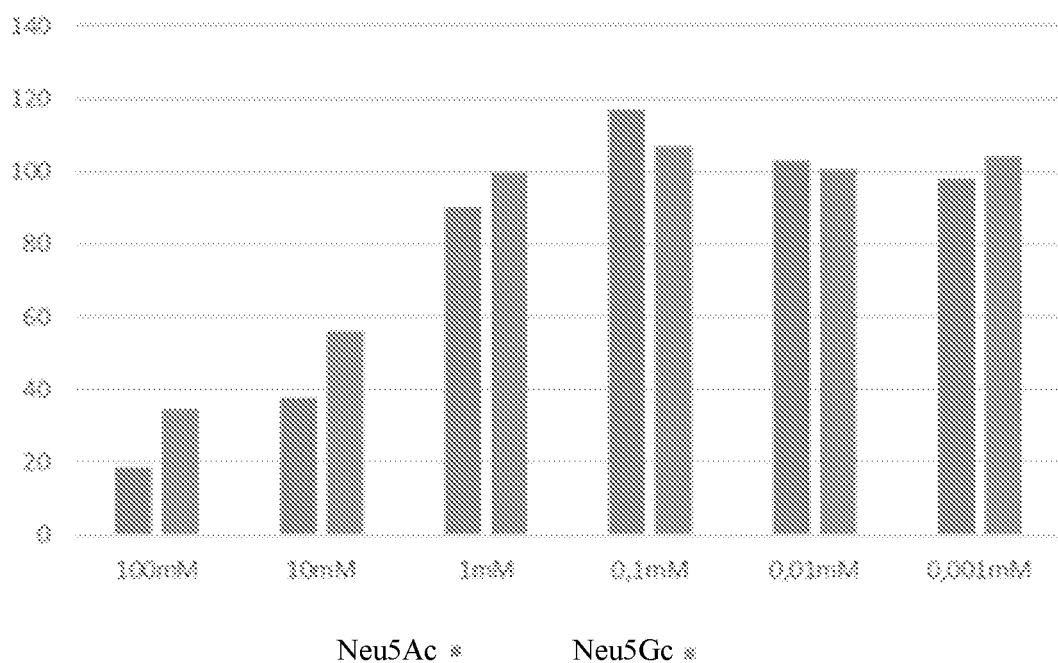
FIG. 1 provides data from one replicate showing infection of cells by CoV-OC43 at different concentrations of either Neu5Ac or Neu5Gc.

The present invention relates to the use of compositions comprising sialic acid to inhibit or treat coronavirus infections, and in particular those caused by SARS-CoV-2 (Severe Acute Respiratory Syndrome Coronavirus 2).

Sialic acid is the generic name for N- or O-substituted derivatives of neuraminic acid, a monosaccharide with nine carbon atoms. The substances were first described in saliva, hence its name after the Greek word saliva: sialon. Sialic acids are found naturally in the end of the dense and complex braid of sugar molecules, proteins and lipids on cell surfaces and on many soluble proteins. Molecular, cellular and genetic studies show that sialic acids participate in the control of cell and cell matrix interactions, intermolecular interactions on cell surfaces and in interactions with other molecules in the cell's immediate extracellular environment 1.

Sialic acids are a family of nine carbon keto-aldononulosonic acids presented at the terminal ends of glycans on cellular membranes. They are abundantly displayed on the surfaces of vertebrate cells, and particularly on all mucosal surfaces. N-acetyl neuraminic acid (Neu5Ac) is the most common form in mammalian cells.

Neu5Ac can be transformed into Neu5Gc with the enzyme CMAH (cytidine monophosphate—N-acetyl-neuraminic acid hydroxylase). This enzyme is not found in humans due to one deletion in the gene encoding it. One assumes therefore that man has in prehistoric times lost the functionality of this gene and thus the ability to transform NeuAc into Neu5Gc. Unlike animals and some others organisms, humans can only synthesize Neu5Ac.

The two most common sialic acids are N-acetyl neuraminic acid (Neu5Ac) and N-glycolylneuraminic acid (Neu5Gc). Carbon atom No. 5 in Neu5AC (square) can be enzymatically modified into one N-acetyl group and further hydroxylated to form Neu5Gc (circle). Hydroxyl group on several carbon atoms (C4, C7; C8 and C9) may further be modified, for example with O-acetyl, O-sulfate, O-lactyl, O-methyl and O-phosphate groups. The sialic acids are attached to carbohydrate chains on glycoproteins and glycolipids via different glucoside bonds. The most common bonds are α2,3 binding to the galactose moiety, α2,6 binding to galactose or to the N-acetylgalactosamine moiety, and α2.8 binding to another sialic acid moiety on a glycan. Sialic acids cleave the airway epithelium—and can act as receptors for viruses. Newer research with glycan microarrays and other sophisticated methods shows the complexity of the interactions between sialic acid-containing receptors on cell surfaces and viruses proteins. This provides opportunities for studies of how viruses adhere to cell surfaces in airway epithelium (4).

According to Schalcter (2017)(5) Neu5Ac is rapidly absorbed after ingestion. It is also quickly excreted via urine. The highest concentration of sialic acids is found in saliva, urine and human brain.

The structure of Neu5Ac, features four protruding functional groups (carboxylate, hydroxyl, N-acetyl and glycerol functions). This large number of functional groups enables sialic acids to participate in a number of hydrogen bonds, salt bridges and non-polar interactions at the same time. Since sialic acid is typically located at the terminus of a glycan, its binding sites are easily accessible for interactions. A large number of viruses, including many serious human pathogens (for example human Influenza A, B and C, Coxsackievirus A24 variant and enterovirus 70, human JC and BK polyomaviruses, Rotaviruses) use sialic acid in sialylated oligosaccharides for cell attachment. Neu et al., Viruses and Sialic Acids: Rules of Engagement. Curr Opin Struct Biol., (2011) 21(5), 610-618).

In most cases, interactions between a viral attachment protein and its glycan receptor involve primarily the sialic acid itself, which is bound with a relatively small contact area in a solvent-exposed region of the virus protein. Consistent with this, the affinities of such interactions are very low. Many of the viruses achieve remarkable specificity for sialylated oligosaccharide by establishing a secondary small number of auxiliary interactions with functional groups that lie beyond the sialic acid. After binding, they use different mechanisms (endocytosis, pinocytosis, fusion) to enter the cell in order to take over the system for virus replication. A recent publication (Tortorici et al., Structural basis for human coronavirus attachment to sialic acid receptors. Nat Struct Mol Biol. 2019 June; 26(6):481-489) proposes the structure of the human Coronavirus site binding to 9-O-acetylated sialic acid at mucosa membrane.

For viruses that are able to multiply and create an infection, viruses should not just stick to epithelial surface, but also enzymatically penetrate the cell to use the cell's own replication machinery. Furthermore, new viral particles may come out of the cell. The "opening" of cell membranes can occur via a neuraminidase—an enzyme that cleaves sialic acid from glycoconjugates. The virus enzyme thus provides for additional spread of new viral particles. Studies have shown that they will also be able to neutralize silicic acid-containing soluble proteins, which will otherwise interfere with surface bonding viruses (6, 7).

Despite many decades of research there are still relatively few effective anti-viral compounds in comparison to the human disease burden inflicted by viruses. Coupled with the high mutation rate of certain viruses, which enable anti-viral resistant mutants to arise with alarming speed and frequency, the need for a generic anti-viral agent is as important now as it ever has been.

Accordingly, provided herein are compositions comprising sialic acid for use in treating or inhibiting infection by SARS-CoV-2. It is contemplated that administration of sialic acid increases the natural content of sialic acid in the nasal mucosa. In some preferred embodiments, the sialic acid is delivered directly to the nasal mucosa via a spray, gel, or other solution containing an effective amount of sialic acid. In some preferred embodiments, the sialic acid is NANA. The present invention is not limited to any particular mechanism of action. Nevertheless, it is contemplated that the administered sialic acid molecules cover the epithelium of the respiratory tract and can act as receptors for "hooking" the viruses. In other words, the free sialic acid molecules (not attached to the nasal mucosa) competitively bind soluble virus particles, thus inhibiting the attachment of virus to the nasal epithelium. Since the free sialic acid is in excess, the binding to cell bound receptors and transport into the cells is lowered, hence the risk of virus infection is decreased and infection is inhibited.

The use of a variety of sialic acids is contemplated. In some embodiments, the sialic acids or sialic acid precursors have a purity selected from the group consisting of greater than 90%, 95%, 99%, and 99.5% pure. In some preferred embodiments, the sialic acid or sialic acid precursor is selected from the group consisting of n-acetylneuraminic acid (NANA), n-glycolylneuraminic acid (NGNA), N-Acetyl-D-mannosamine, and combinations thereof. In other preferred embodiments, the composition may comprise one or more of the following sialic acids: Neuraminic acid, 5-N-Acetyl-4-O-acetyl-neuraminic acid, 5-N-Acetyl-7-O-acetyl-neuraminic acid, 5-N-Acetyl-8-O-acetyl-neuraminic acid, 5-N-Acetyl-9-O-acetyl-neuraminic acid, 5-N-Acetyl-4,9-di-O-acetyl-neuraminic acid, 5-N-Acetyl-7,9-di-O-acetyl-neuraminic acid, 5-N-Acetyl-8,9-di-O-acetyl-neuraminic acid, 5-N-Acetyl-7,8,9-tri-O-acetyl-neuraminic acid, 5-N-Acetyl-9-O-L-lactyl-acetyl-neuraminic acid, 5-N-Acetyl-4-O-acetyl O-lactyl-acetyl-neuraminic acid, 5-N-Acetyl-8-O-methyl-neuraminic acid, 5-N-Acetyl-9 acetyl-8-O-methyl-neuraminic acid, 5-N-Acetyl-8-O-sulpho-neuraminic acid, 5-N-Acetyl O-phosphoro-neuraminic acid, 5-N-Acetyl-2-deoxy-2,3-didehydro-neuraminic acid, 5-N-Acetyl-9-O-acetyl-2-deoxy-2,3-didehydro-neuraminic acid, 5-N-Acetyl-2-deoxy-2,3-didehydro-9-O-lactyl-neuraminic acid, 5-N-Acetyl-2,7-anhydro-neuraminic acid, 4-O-Acetyl-5-N-glycolyl-neuraminic acid, 7-O-Acetyl-5-N-glycolyl-neuraminic acid, 8-O-Acetyl-5-N-glycolyl-neuraminic acid, 9-O-Acetyl-5-N-glycolyl-neuraminic acid, 7,9-Di-O-acetyl-5-N-glycolyl-neuraminic acid, 8,9-Di-O-acetyl-5-N-glycolyl-neuraminic acid, 7,8,9-Tri-O-acetyl-5-N-glycolyl-neuraminic acid, 5-N-glycolyl-9-O-lactyl-neuraminic acid, 5-N-glycolyl-8-O-methyl-neuraminic acid, 9-O-Acetyl-5-N-glycolyl-8-O-methyl-neuraminic acid, 7,9-di-O-Acetyl-5-N-glycolyl-8-O-methyl-neuraminic acid, 5-N-glycolyl-8-O-sulpho-neuraminic acid, N-(O-acetyl)glycolylneuraminic acid, N-(O-Methyl)glycolylneuraminic acid, 2-Deoxy-2,3-didehydro-5-N-glycolyl-neuraminic acid, 9-O-Acetyl-2-deoxy-2,3-didehydo-5-N-glycolyl-neuraminic acid, 2-Deoxy-2,3-didehydro-5-N-glycolyl-9-O-lactyl-neuraminic acid, 2-Deoxy-2,3-didehydro-5-N-glycolyl-8-O-methyl-neuraminic acid, 2,7-Anhydro-5-N-glycolyl-neuraminic acid, 2,7-Anhydro-5-N-glycolyl-8-O-methyl-neuraminic acid, 2-Keto-3-deoxynononic acid, and 9-O-Acetyl-2-keto-3-deoxynononic acid.

In some particularly preferred embodiments, the sialic acid is NANA.

Exemplary formulations are described in detail below. However, in some embodiments, the sialic acid is formulated as a lotion, spray, gel, ointment, powder, aqueous or non-aqueous solution for topical, intranasal, intravaginal, intraanal, or sublingual administration; as a capsule, powder, or tablet for enteral administration; or as a solution for parenteral administration.

Sialic compositions of the present invention may be delivered in any suitable format. In some embodiments, the sialic acid is preferably about greater than 90%, 95%, 99% or 99.9% pure. In some embodiments, the sialic acid is HPLC purified. For example, NANA can be purchased commercially from, for example, Sigma Chemical Company, St. Louis, Mo.

In some embodiments, the present invention provides methods of treating, alleviating, ameliorating, or inhibiting infection by a SARS-CoV-2, or reducing symptoms or outbreaks associated with infection by SARS-CoV-2, comprising administering an effective concentration of sialic acid (e.g., NANA). In some preferred embodiments, an effective concentration of sialic acid (e.g., NANA) is from about 0.1 to about 10 mg/ml in an aqueous solution, for example, for treating, alleviating, ameliorating, reducing or inhibiting infection by SARS-CoV-2 or symptoms associated with SARS-CoV-2. In some preferred embodiments, the effective concentration of sialic acid (e.g., NANA) is from about 0.5 to about 100 mg/ml in an aqueous solution. In some preferred embodiments, the effective concentration of sialic acid (e.g., NANA) is from about 0.5 to about 50 mg/ml in an aqueous solution. In some preferred embodiments, the effective concentration of sialic acid (e.g., NANA) is from about 0.5 to about 5 mg/ml in an aqueous solution. In some preferred embodiments, the daily dosage of sialic acid (e.g., NANA) is from about 0.1 to 5.0 mg sialic acid (e.g., NANA)/nostril/day. In some preferred embodiments, the daily dosage of sialic acid (e.g., NANA) is from about 0.1 to 1.0 mg sialic acid (e.g., NANA)/nostril/day. In some preferred embodiments, the effective concentration of sialic acid (e.g., NANA) is from about 0.5 to about 100 mg/ml in an aqueous solution. In some preferred embodiments, the daily dosage of sialic acid (e.g., NANA) is from about 0.1 to 100 mg sialic acid (e.g., NANA)/nostril/day. In some preferred embodiments, the daily dosage of sialic acid (e.g., NANA) is from about 0.1 to 50 mg sialic acid (e.g., NANA)/nostril/day.

In some preferred embodiments, the pH of composition comprising the sialic acid (e.g., NANA), preferably in aqueous solution, is from 2.0 to 4.0. In some preferred embodiments, the pH of composition comprising the sialic acid (e.g., NANA), preferably in aqueous solution, is from 2.5 to 3.7. In some preferred embodiments, the pH of composition comprising the sialic acid (e.g., NANA), preferably in aqueous solution, is from 2.8 to 3.2.

In some embodiments, the sialic acid (e.g., NANA) compositions are provided in an aqueous solution, including gels, suitable for use as a spray or mist. In some embodiments, the aqueous sialic acid (e.g., NANA) solution is incorporated into a pump-spray container, such as precompression pump, or a device such as a nebulizer or cold mist system, for delivery into the nose, mouth or lungs as a fine mist or spray. In some preferred embodiments, the present invention provides a spray bottle configured for application of a nasal spray to the nose of animal or human containing any of the compositions described above.

In some preferred embodiments, the daily dosage of sialic acid (e.g., NANA) is from about 0.1 to 5.0 mg sialic acid (e.g., NANA) nostril/day. In some preferred embodiments, the daily dosage of NANA is from about 0.1 to 1.0 mg sialic acid (e.g., NANA)/nostril/day. In some preferred embodiments, the spray bottle is calibrated to deliver a spray dose comprising from 0.03 to 1.0 mg sialic acid (e.g., NANA)/spray. In some preferred embodiments, the spray bottle is calibrated to deliver a spray dose comprising from 0.05 to 0.3 mg sialic acid (e.g., NANA)/spray. In some preferred embodiments, the daily dosage of sialic acid (e.g., NANA) is delivered in from 2 to 8 administrations per day from the spray bottle, i.e., from 2 to 8 pumps of the spray to each nostril.

In some preferred embodiments, the daily dosage of sialic acid (e.g., NANA) is from about 0.1 to 100 mg sialic acid (e.g., NANA) nostril/day. In some preferred embodiments, the daily dosage of NANA is from about 1.0 to 100 mg sialic acid (e.g., NANA)/nostril/day. In some preferred embodiments, the spray bottle is calibrated to deliver a spray dose comprising from 1.0 to 100 mg sialic acid (e.g., NANA)/spray. In some preferred embodiments, the spray bottle is calibrated to deliver a spray dose comprising from 1.0 to 50 mg sialic acid (e.g., NANA)/spray. In some preferred embodiments, the daily dosage of sialic acid (e.g., NANA) is delivered in from 2 to 8 administrations per day from the spray bottle, i.e., from 2 to 8 pumps of the spray to each nostril.

In some embodiments, the composition further comprises a thixotropic agent (e.g., including but not limited to, fucoidans, alginates or chitosan). In some embodiments, the thixotropic agent is mannuronic acid. In some embodiments, the mannuronic acid is present in the composition at a w/w percent range of 0.01 to 2.0% (e.g., 0.01 to 1.0% or 0.1% to 0.5%).

In some embodiments, the sialic acid (e.g., NANA) compositions of the present invention contain a pharmaceutically acceptable excipient which is effective in forming a thixotropic suspension of the solid particles of medicament comprising the composition, such as those described in U.S. Pat. No. 7,122,206. The excipient is preferably present in an amount which maintains the particles of medicament suspended in the composition during non-use and during spray of the composition into the nasal cavity, and also when the composition is deposited on the mucosal surfaces of the nasal cavities or endothelial surfaces in the nasal cavity or elsewhere in the body. In some embodiments, the viscosity of the composition at rest is relatively high, for example, about 400 to about 1000 cp. As the composition is subjected to shear forces, for example, upon being subjected to forces involved in its being agitated before spraying, the viscosity of the composition decreases (for example, to about 50 to about 200 cp) and it flows readily through the spray device and exits therefrom in the form of a fine plume which infiltrates and deposits on the mucosal surfaces of at least the following parts of the nose: the anterior regions of the nose (frontal nasal cavities); the frontal sinus; the maxillary sinuses; and the turbinates which overlie the conchas of the nasal cavities. Thus, the NANA compositions comprise a freely flowable liquid, and in sprayed form, a fine mist that finds its way to and deposits on the desired mucosa. In deposited and relatively unstressed form, the composition increases in viscosity and assumes its gel-like form which includes particles of the medicament suspended therein and which resists being cleared from the nasal passages by the inherent mucocillary forces that are present in the nasal cavities.

Any pharmaceutically acceptable material which is capable of maintaining the solid particles of medicament dispersed substantially uniformly in the composition and of imparting to the composition desired thixotropic properties can be used. Such material is referred to as a "suspending agent". Examples of suspending agents include carboxmethylcellulose, veegum, tragacanth, bentonite, methylcellulose, and polyethylene glycols. A preferred suspending agent is a mixture of microcrystalline cellulose and carboxymethylcellulose, the former being present preferably in a major amount, most preferably in an amount of about 85 to about 95 wt. %, with the latter constituent comprising about 5 to about 15 wt. % of the mixture.

The amount of suspending agent comprising the composition will vary depending on the particular medicament and amount used, the particular suspending agent used, the nature and amounts of the other ingredients comprising the composition, and the particular viscosity values that are desired. Generally speaking, it is believed that the most widely used compositions will comprise about 1 to about 5 wt. % of the suspending agent.

The sialic acid (e.g., NANA) compositions of the present invention includes preferably other ingredients which impart desired properties to the composition. In some embodiments, dispersing or wetting agents are utilized. Any dispersing agent which is effective in wetting the particles and which is pharmaceutically acceptable can be used. Examples of dispersing agents that can be used are fatty alcohols, esters, and ethers, including, for example, those sold under the trademarks Pluronic, Tergitol, Span, and Tween. It is preferred to use a hydrophilic, non-ionic surfactant. Excellent results have been achieved utilizing sorbitan monooleatepolyoxyethylene which is available under the trademark Polysorbate 80.

In some embodiments, the compositions comprise an anti-oxidant. Examples of pharmaceutically acceptable antioxidants that can be used in the composition include ascorbic acid, sodium ascorbate, sodium bisulfite, sodium thiosulfate, 8-hydroxy quinoline, and N-acetyl cysterine. It is recommended that the composition comprise about 0.001 to about 0.01 wt. % of the anti-oxidant.

Also, for stability purposes, the sialic acid (e.g., NANA) compositions should be protected from microbial contamination and growth. Examples of pharmaceutically acceptable anti-microbial agents that can be used in the composition include quaternary ammonium compounds, for example, benzalkonium chloride, benzethonium chloride, cetrimide, and cetylpyridinium chloride; mercurial agents, for example, phenylmercuric nitrate, phenylmercuric acetate, and thimerosal; alcoholic agents, for example, chlorobutanol, phenylethyl alcohol, and benzyl alcohol; antibacterial esters, for example, esters of para-hydroxybenzoic acid; and other anti-microbial agents such as chlorhexidine, chlorocresol, and polymyxin. It is recommended that the composition comprise about 0.001 to about 1 wt. % of the anti-microbial agent.

As mentioned above, an aspect of the present invention comprises a composition which is odorless and which contains a mixture of stabilizing agents which function as an anti-oxidant and as an anti-microbial agent. The mixture comprises a quaternary ammonium compound that has anti-microbial properties and a material which is generally recognized as a chelating agent. The use in the composition of this combination of materials with the medicament, for example, triamcinolone acetonide, results in a highly stable composition that is resistant to oxidative degradation and to the growth of bacteria and the like. In preferred form, the mixture comprises benzalkonium chloride and disodium ethylenediamine tetraacetate.

The odorless composition generally will comprise about 0.004 to about 0.02 wt. % of the quaternary ammonium compound and about 0.01 to about 0.5 wt. % of the chelating agent. By virtue of the use of the aforementioned mixture of compounds, it is not necessary to include in the composition a material which is considered an anti-oxidant.

The composition of the present invention includes preferably an iso-osmotic agent which functions to prevent irritation of nasal mucosa by the composition. Dextrose in anhydrous form is a preferred iso-osmotic agent. Examples of other pharmaceutically acceptable iso-osmotic agents which can be used include sodium chloride, dextrose and calcium chloride. It is recommended that the composition comprise up to about 5 wt. % of the iso-osmotic agent.

The sialic acid (e.g., NANA) compositions of the present invention can be prepared in any suitable way. In preferred form, an aqueous suspension of the solid particles of medicament and dispersing agent is formed and combined with an aqueous suspension which contains the suspending agent. The former is preferably prepared by adding the medicament to an aqueous solution of the dispersing agent and mixing thoroughly. The latter is prepared by acidifying the water (pH about 4.7 to about 5.3) prior to adding the suspending agent. In particularly preferred form, an aqueous solution of the quaternary compound (anti-microbial agent) is added to the aqueous suspension of medicament, and the other ingredients (for example, iso-osmotic agent, anti-oxidant or chelating agent) are added to the thixotropic suspension. Each of the aforementioned batches of composition is mixed thoroughly before being combined. The preferred means of combining the batches of composition is to introduce one of the batches, preferably the "medicament" batch into the bottom of the other batch, for example, by pumping the batch upwardly through the other batch. The composition comprising the combined batches is mixed thoroughly. Use of the preferred method of preparation provides an efficient and effective way for formulating a composition that has the solid particles of medicament substantially uniformly dispersed therein while avoiding problems that are generally associated with the preparation of water-based pharmaceutical compositions, for example, excessive foaming and non-uniformity of the particle dispersement.

The amount of sialic acid (e.g., NANA) applied to each of the nasal passages will vary depending on the nature of the condition being treated and the nature of the individual being treated. In some preferred embodiments, the effective concentration of sialic acid (e.g., NANA) is from about 0.1 to about 100 mg/ml in an aqueous solution. In some preferred embodiments, the effective concentration of sialic acid (e.g., NANA) is from about 1.0 to about 100 mg/ml in an aqueous solution. In some preferred embodiments, the effective concentration of sialic acid (e.g., NANA) is from about 1.0 to about 50 mg/ml in an aqueous solution. In some preferred embodiments, the effective concentration of sialic acid (e.g., NANA) is from about 0.1 to about 10 mg/ml in an aqueous solution. In some preferred embodiments, the effective concentration of sialic acid (e.g., NANA) is from about 0.5 to about 5 mg/ml in an aqueous solution. In some preferred embodiments, the daily dosage of sialic acid (e.g., NANA) is from about 0.001 to 0.1 mg sialic acid (e.g., NANA)/nostril/day. In some preferred embodiments, the daily dosage of sialic acid (e.g., NANA) is from about 0.01 to 0.05 mg sialic acid (e.g., NANA)/nostril/day. In some preferred embodiments, the daily dosage of sialic acid (e.g., NANA) is delivered in from 2 to 8 administrations per day.

Accordingly, the present invention provides an article of manufacture comprising a spray bottle having an sialic acid (e.g., NANA) solution or powder therein for delivery into a body cavity such as the nose. The spray bottle may preferably comprise a pump system for expelling the NANA composition from the bottle, such as a compression mump, spray pump or precompression pump. In some preferred embodiments, the spray bottle is calibrated to deliver a spray dose comprising from 0.1 to 10 mg sialic acid (e.g., NANA)/spray. In some preferred embodiments, the spray bottle is calibrated to deliver a spray dose comprising from 0.001 to 0.02 mg sialic acid (e.g., NANA)/spray. In some preferred embodiments, the spray bottle is calibrated to deliver a spray dose comprising from 0.004 to 0.01 mg sialic acid (e.g., NANA)/spray.

In some embodiments, the present invention provides an article of manufacture that is a device that can be worn over a body cavity such as the mouth or nose of an individual. In some embodiments, the device is mask, such as a surgical mask. In preferred embodiments, the mask comprises a solid support or matrix, such as a polymer matrix or a woven fabric matrix, into which an sialic acid (e.g., NANA) composition is incorporated. In some embodiments, the sialic acid (e.g., NANA) composition is spray coated onto the matrix as an aqueous solution, gel or powder. In some embodiments, when a breath is taken through the mask, viruses are inactivated as they contact the mask. In some embodiments, the matrix is coated with an sialic acid (e.g., NANA) composition to provide from about 0.01 microgram to about 100 milligram sialic acid (e.g., NANA) per cm$^2$ of the matrix, preferably from about 1 microgram to about 1 milligram sialic acid (e.g., NANA) per $cm^2$.

In some embodiments, sialic acid (e.g., NANA) is formulated for oral delivery. The ingredients of the supplements of this invention are preferably contained in acceptable excipients and/or carriers for oral consumption. The actual form of the carrier, and thus, the supplement itself, is not critical. The carrier may be a liquid, gel, gelcap, capsule, powder, solid tablet (coated or non-coated), tea, or the like. The supplement is preferably in the form of a tablet or capsule and most preferably in the form of a hard gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of *Remington's Pharmaceutical Sciences* (Maack Publishing Co., Easton, Pa.).

In some embodiments, the oral delivery vehicles described above are formulated so as to provide a daily dose of between 0.1 g and 10.0 g of sialic acid (e.g., NANA), preferably between 0.5 and 2.0 g of NANA, and even more preferably approximately 1.0 g of sialic acid (e.g., NANA). In some embodiments, an effective amount of NANA is the amount needed to inhibit the growth and proliferation of a virus of interest or to inactivate the virus. In some embodiments, the effective amount is the amount of sialic acid (e.g., NANA) sufficient to provide a concentration of NANA of from about 1 nanomolar to 10 micromolar at a site of interest, such as the circulating bloodstream or in a body cavity such as the nasal passages or sinuses.

In some preferred embodiments, the sialic acid is administered orally. In some preferred embodiments, the daily dosage of sialic acid is from 20 to 200 grams. In some preferred embodiments, the daily dosage of sialic acid is from 50 to 150 grams. In some preferred embodiments, the daily dosage is administered in from 1 to 20 doses. In some preferred embodiments, the sialic acid is administered as a aqueous solution. In some preferred embodiments, the aqueous solution comprising an additional agent selected from the group consisting of a flavoring agent, a stabilization agent and a preservative agent, wherein the additional agent does not naturally occur with sialic acid.

In some embodiments, sialic acid (e.g., NANA) is provided in a fluid that can be used for atmospheric treatment, such as by a mist. In some embodiments, the present invention provides a device comprising a reservoir, a pump, and a nozzle, wherein the reservoir comprises a fluid comprising sialic acid (e.g., NANA) that can be expelled via the pump through the nozzle to provide a mist comprising sialic acid (e.g., NANA). In some embodiments, the device is a humidifier, while in other embodiments, the device is an automated mist dispenser. In some embodiments, the sialic acid (e.g., NANA) is provided as an aerosol spray in an appropriate aerosol spray dispensing device. Accordingly, in some embodiments, the present invention provides a device or composition comprising a sialic acid (e.g., NANA) and an aerosol propellant. Propellants include, but are not limited to, mixtures of volatile hydrocarbons, typically propane, n-butane and isobutene, dimethyl ether (DME), methyl ethyl ether, nitrous oxide, carbon dioxide and hydrofluoroalkanes (HFA): either HFA 134a (1,1,1,2,-tetrafluoroethane) or HFA 227 (1,1,1,2,3,3,3-heptafluoropropane) or combinations of the two. Typically, the sialic acid (e.g., NANA) fluid will be miscible with the propellant. The sialic acid (e.g., NANA) fluid may preferably be formulated to be an aerosol mist, foaming gel, cream or lotion.

Modern aerosol spray products have three major parts; the can, the valve and the actuator or button. The can is most commonly lacquered tinplate (steel with a layer of tin) and may be made of 2 or 3 pieces of metal crimped together. Aluminum cans are also common and are generally used for more expensive products. The valve is crimped to the rig of the can, the design of this component is important in determining the spray rate. The actuator is depressed by the user to open the valve; the shape and size of the nozzle in the actuator controls the spread of the aerosol spray.

In some embodiments, the devices of the present invention comprise a piston barrier system. Packaging that uses a piston barrier system is often used for highly viscous products such as post-foaming gels, thick creams and lotions. The main benefit of the piston barrier system is that is assures separation of the product from the propellant, maintaining the purity and integrity of the formulation throughout its consumer lifespan. The piston barrier system also provides a controlled and uniform product discharge rate with minimal product retention and is economical.

In some embodiments, the devices of the present invention comprise a bag-in-can system (or BOV "bag on valve"). This system separates the product from the pressurizing agent with a hermetically-sealed, multi-layered laminated pouch, which maintains complete formulation integrity so only pure product is dispensed. In this embodiment, the NANA fluid is provided in the bag. Among its many benefits, the bag-in-can system extends a product's shelf life. Other advantages include all-attitude (360-degree) dispensing, quiet and non-chilling discharge.

These devices find use in setting where an antiviral spray, foam, gel or other fluid is needed. For example, the devices find use in dispensing an antiviral mist to treat a desired environment or space, such as a room in a building such as an office, kitchen, cubicle or lavatory, or a vehicle such a train car, airplane, bus, or taxi, van or car, or animal confinement facilities such as barns, abattoirs, poultry houses, etc. The devices can also be used to dispense sialic acid (e.g., NANA) containing fluids on a surface such as a countertop, floor, shower, etc. In some embodiments, the devices are used to inject the sialic acid (e.g., NANA)—containing mist into the ventilation system of a building, barn, or vehicle.

In still further embodiments, the present invention provides sialic acid (e.g., NANA) compositions that comprise sialic acid (e.g., NANA) in a solution, such as a normal saline solution, that can be applied to the eye. Accordingly, in some embodiments, the present invention provides an article of manufacture comprising a container equipped with a nozzle to provide drops of an sialic acid (e.g., NANA)

solution to the eye. It is contemplated that in addition to effects in the eye and surrounding tissue, sialic acid (e.g., NANA) administration via the eye and tear channel will directly access the sinuses and associated cavities. Thus, administration of sialic acid (e.g., NANA) and/or additional antimicrobials or antivirals in eyedrops is an effective method of administration of sialic acid (e.g., NANA) or other compounds for the treatment of eye infections, sinus infections, and systemic treatment via the eye and tear channel, and sinuses, mucus internal surfaces for effective adsorption providing local and systemic treatments.

In other embodiments, the sialic acid (e.g., NANA) is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

In some embodiments, the sialic acid (e.g., NANA) is provided in water that is supplied to farm animals, such as poultry, cattle, swine, sheep and the like, or used in water used in fisheries. In other embodiments, sialic acid (e.g., NANA) is provided in tap water or water bottles water for human use.

The sialic acid (e.g., NANA) compositions may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the compositions of the present invention may contain one or more of the following: asorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the compositions further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

The present invention provides dietary supplements comprising nutraceutical agents, preferably sialic acid (e.g., NANA) either by itself or in combination with one or more additional nutraceuticals agents. Nutraceutical agents are natural, bioactive chemical compounds that have health promoting, disease preventing or medicinal properties. Examples of nutraceuticals include, but are not limited to, *Allium cepa*, *Allium sativum*, *Aloe vera*, *Angelica* Species, Naturally Occurring Antioxidants, *Aspergillus oryzae* Enzyme Therapy, barley grass, Bromelain, Carnitine, Carotenoids and Flavonoids, Catechin, Centella *Asiatica* (Gotu kola), Coenzyme Q10, Chinese Prepared Medicines, *Coleus forskohlii*, *Commiphora mukul*, Conjugated Linoleic Acids (CLAs), *Crataegus oxyacantha* (Hawthorne), *Curcuma longa* (Turmeric), *Echinacea* Species (Purple Coneflower), *Eleutherococcus senticosus* (Siberian *Ginseng*), *Ephedra* Species, Dietary Fish Oil Consumption and Fish Oil Supplementation, Genistein, *Ginkgo biloba*, *Glycyrrhiza* (Licorice), *Hypericum* Perforatum (St. John's Wort), *Hydrastis* (Goldenseal) and Other Berberine-Containing Plants, *Lactobacillus*, *Lobelia* (Indian Tobacco), *Melaleuca Alternifolia*, *Menaquinone*, *Mentha piperita*, *Panax ginseng*, Pancreatic Enzymes, Piper Mythisticum, Procyanidolic Oligomers, *Pygeum africanum*, Quercetin, Sarsaparilla Species, *Serenoa repens* (Saw palmetto, *Sabal serrulata*), *Silybum marianum* (Milk Thistle), Rosemary/Lemon balm, Selenite, *Tabebuia avellanedae* (LaPacho), *Taraxacum officinale*, *Tanacetum parthenium* (Feverfew), Taxol, *Uva ursi* (Bearberry), *Vaccinium myrtillus* (Blueberry), *Valerian officinalis*, *Viscum album* (Mistletoe), Vitamin A, Beta-Carotene and Other Carotenoids, and *Zingiber officinale*(Ginger).

Several nutraceutical agents are used in treating viral disorders (e.g., Genistein (in soy/red clover), rosemary/lemon balm, selenite, barley grass, lauric acid, *Phyllanthus amarus/niruri* (see, e.g., Nicolson, G. (1998) J. Medicine 1:123-128; herein incorporated by reference in its entirety). Additional anti viral nutraceutical agents include, but are not limited to, catechins, flavonoids, *Echinacea*, and cascara.

EXAMPLES

Example 1

A nasal spray is formulated that comprises 1 mg/ml n-acetylneuraminic acid (NANA) in a sterile 0.9% saline solution with a pH of 3.0. The formulation may be provided in a 20 ml pump spray bottle calibrated to deliver an average of 140 sprays with 1 spray being delivered for each pump of the bottle.

Example 2

A nasal spray is formulated that comprises 1 mg/ml n-glycolylneuraminic acid (NGNA) in a sterile 0.9% saline solution with a pH of 3.0. The formulation may be provided in a 20 ml pump spray bottle calibrated to deliver an average of 140 sprays with 1 spray being delivered for each pump of the bottle.

Example 3

Figure 2:
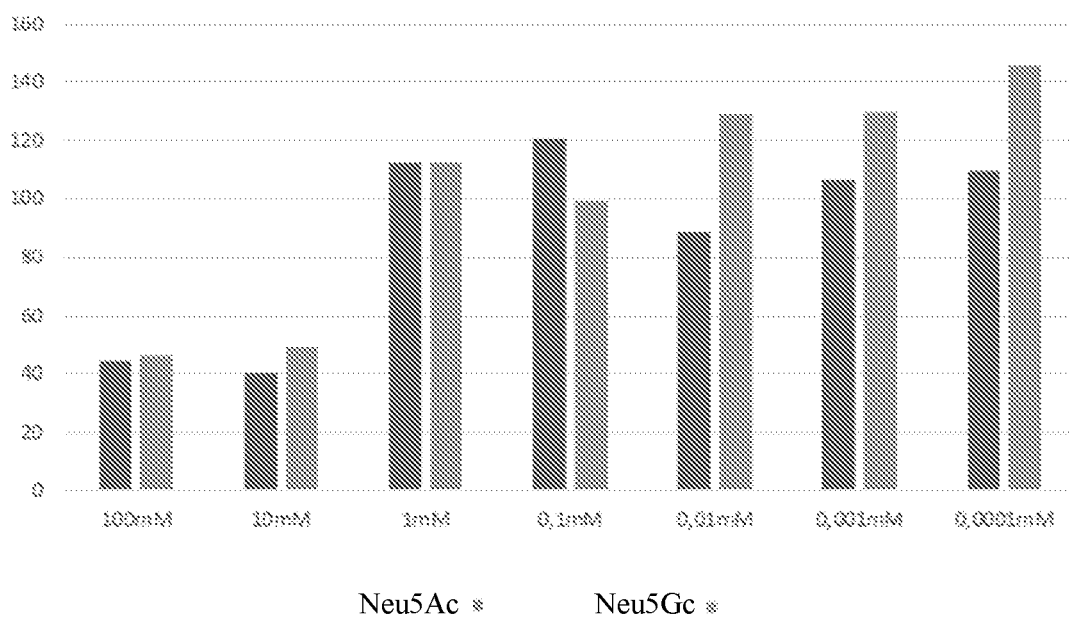
FIG. 2 provides data from another replicate showing infection of cells by CoV-OC43 at different concentrations of either Neu5Ac or Neu5Gc.
Figure 3:
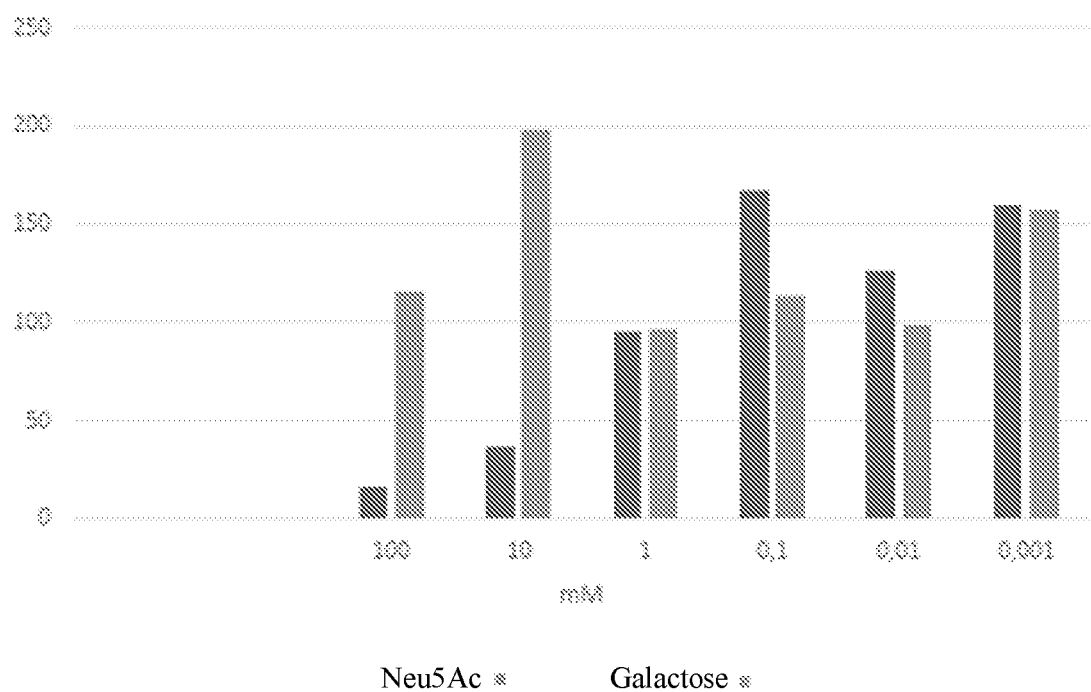
FIG. 3 provides data from an experiment where inhibition of infection by Neu5Ac is compared to a control sugar, galactose.

The effectiveness of sialic acid (Neu5Ac or Neu5Gc) in preventing corona virus infection was evaluated in vitro in a model system. Different dilutions of the sialic acids were tested for their ability to inhibit infection of cells with the test virus CoV-OC43. The results are presented in FIGS. 1 to 3. FIGS. 1 and 2 provide data from two replicates showing infection of cells by CoV-OC43 at different concentrations of either Neu5Ac or Neu5Gc (Neu5Ac left hand bars, Neu5Gc right hand bars). As can be seen, infection is inhibited in a dose-dependent manner. FIG. 3 provides data from an experiment where inhibition of infection by Neu5Ac (left hand bars) is compared to a control sugar, galactose (right hand bars). As can be seen, Neu5Ac prevents infection as compared to the control.

REFERENCES

1. Ronald L. Schnaars, Rita Gerardy-Schahn, and Herbert Hildebrandt: sialic Acids in the Brain: Gangliosides and Polysialic Acid Nervous System Development, Stability, Disease, and Regeneration. Physiol Rev. 2014 April; 94 (2): 461-518.doi: 10.1152/physrev.00033.2013
2. Norbert Sprenger and Peter I. Duncan: sialic Acid Utilization. 2012 American Society for Nutrition. Adv. Nutr. 3: 392S-397S, 2012; doi: 10.3945/m.111.001479.
3. Jennifer E. Stencel-Baerenwald, Kerstin Reiss, Dirk M. Reiter, Thilo Stehle, and Terence S. Dermody: The sweet spot: Defining virus-sialic acid interactions. Nat Rev Microbiol. 2014 November; 12 (11): 739-749. doi: 10.1038/nrmicro3346.

3 B Wang and J Brand-Miller: The role and potential of sialic acid in human nutrition. Review.

4 Ursula Neu, Johannes Bauer, and Thilo Stehle. Viruses and sialic Acids: Rules of Engagement. Curr Opin Struct Biol. 2011 October; 21 (5): 610-618. doi: 10.1016/j.sbi.2011.08.009.

5 Schalcter M: N-Acetylneuraminic Acid (Neu5Ac). www.glyconutritionforlife.org/Science of Glyconutrients/N-Acetylneuraminic Acid_(Neu5Ac) php 6 Ajit Varki, sialic acids in human health and disease. Trends Mol Med. 2008 August; 14 (8): 351-360. doi: 10.1016/j.molmed.2008.06.002.

7 Thilo Stehle, Zaigham M. Khan: Rules and Exceptions: sialic Acid Variants and Their Role in Determining Viral Tropism. Journal of Virology p. 7696-7699 July 2014 Volume 88 Number 14

8 Muriel Bardor, Dzung H. Nguyen, Sandra Diaz, and Ajit Varki: Mechanism of Uptake and Incorporation of the Non-human sialic acid N-Glycolylneuraminic Acid into Human Cells. J Biol Chem Vol. 280, No. 6, Issue of February 11, pp. 4228-4237, 2005

9 Newburg, D S: Do the binding properties of oligosaccharides in milk protect human infants from gastrointestinal bacteria? J. Nutr. 127: 980S-984S, 1997.

10 Heine, W; Wutzke, K D; Radke M. Sialic acid in breast milk and infant formula food. Monatsschr Kinderheilkd. 1993 December; 141 (12): 946 to −50.

11 Boehm, G and Stahl, B. Oligosaccharides in milk. J. Nutr 2007, vol 137, p 847S-849S 12 Martin-Sosa, S, Martin, M-J and Hueso, P: The Sialylated Fraction of Milk oligosaccharides Ice Partially Responsible for Binding two enterotoxigenic and Uropathogenic *Escherichia coli* Human Strains. J. Nutr. 132: 3067-3072, 2002

13 Samraj A N, Pearce O M, Laubli H, Crittenden A N, Bergfeld A K, Banda K, Gregg C J, Bingman A E, Secrest P, Diaz S L, Varki N M, Varki A.: A red meat-derived glycan promoter inflammation and cancer progression. Proc Natl Acad Sci US A. 2015 Jan. 13; 112 (2): 542 to −7. doi:10.1073/pnas.1417508112. Epub 2014 Dec. 29.

14 GRAS Notice (GRN) No. 602 http://www.fda.gov/Food/IngredientsPackagingLabeling/GRAS/NoticeInventory/default.htm ORIGINAL SUBMISSION 15 Choi, S H, Baldin, N., Wagner, V O (2I), Roy, S., Rose, J., Thosrud, B A, Pnothirath, P. & Řorigh, CH 2014. Safety evaluation of the human-identical milk monosaccharide sialic acid (N-acetyl-D-neuraminic acid) in Sprague-Dawley rats. Regul. Toxicol. Pharmacol., 70, 482 to −491.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

I claim:

1. A method for treating or inhibiting infection by SARS-CoV-2 (Severe Acute Respiratory Syndrome Coronavirus 2), in a human or animal subject, the method comprising:

administering a composition comprising n-acetylneuraminic acid (NANA) in an effective concentration to the subject under conditions such that infection by SARS-CoV-2 is inhibited or treated.

2. A method for prophylaxis of infection by SARS-CoV-2 (Severe Acute Respiratory Syndrome Coronavirus 2), in a human or animal subject, the method comprising:

administering a composition comprising n-acetylneuraminic acid (NANA) in an effective concentration to the subject under conditions such that infection by SARS-CoV-2 is inhibited.

3. Method of claim 1, wherein the composition comprising n-acetylneuraminic acid (NANA) is administered intranasally.

4. Method of claim 3, wherein the composition is an aqueous solution and the effective concentration of n-acetylneuraminic acid (NANA) is from about 0.1 to about 100 mg/ml in the aqueous solution.

5. Method of claim 3, wherein the composition is an aqueous solution and the effective concentration of n-acetylneuraminic acid (NANA) is from about 0.5 to about 50 mg/ml in the aqueous solution.

6. Method of claim 4, wherein the composition comprising n-acetylneuraminic acid (NANA) is administered in a daily dosage of from about 0.1 to 100 mg NANA/nostril/day.

7. Method of claim 4, wherein the composition comprising n-acetylneuraminic acid (NANA) is administered in a daily dosage of from about 0.1 to 10 mg NANA/nostril/day.

8. Method of claim 4, wherein the pH of the aqueous solution is from 2.0 to 4.0.

9. Method of claim 4, wherein the pH of the aqueous solution is from 2.5 to 3.7.

10. Method of claim 4, wherein the pH of the aqueous solution is from 2.8 to 3.2.

11. Method of claim 4, wherein the effective concentration of n-acetylneuraminic acid (NANA) is delivered in from 2 to 8 administrations per day.

12. Method of claim 4, wherein the composition further comprises a thixotropic agent.

13. Method of claim 1, wherein the composition comprising n-acetylneuraminic acid (NANA) is administered orally.

14. Method of claim 13, wherein the composition comprising n-acetylneuraminic acid (NANA) is administered in a daily dosage of from 20 to 200 grams n-acetylneuraminic acid (NANA).

15. Method of claim 13, wherein composition comprising n-acetylneuraminic acid (NANA) is administered in a daily dosage of from 50 to 150 grams n-acetylneuraminic acid (NANA).

16. Method of claim 13, wherein the composition comprising n-acetylneuraminic acid (NANA) is administered in from 1 to 20 doses.

17. Method of claim 13, wherein the n-acetylneuraminic acid (NANA) is administered as an aqueous solution.

18. Method of claim 17, wherein the aqueous solution comprises an additional agent selected from the group consisting of a flavoring agent, a stabilization agent and a preservative agent, wherein the additional agent does not naturally occur with sialic acid.

19. The method of claim 1, wherein the subject is at risk for infection by SARS-CoV-2.

20. The method of claim 1, wherein the subject has COVID-19.

21. Method of claim 2, wherein the composition comprising n-acetylneuraminic acid (NANA) is administered intranasally.

22. Method of claim 21, wherein the composition is an aqueous solution and the effective concentration of n-acetylneuraminic acid (NANA) is from about 0.1 to about 100 mg/ml in the aqueous solution.

23. Method of claim 21, wherein the composition is an aqueous solution and the effective concentration of n-acetylneuraminic acid (NANA) is from about 0.5 to about 50 mg/ml in the aqueous solution.

24. Method of claim 22, wherein the composition comprising n-acetylneuraminic acid (NANA) is administered in a daily dosage of from about 0.1 to 100 mg NANA/nostril/day.

25. Method of claim 22, wherein the composition comprising n-acetylneuraminic acid (NANA) is administered in a daily dosage of from about 0.1 to 10 mg NANA/nostril/day.

26. Method of claim 22, wherein the pH of the aqueous solution is from 2.0 to 4.0.

27. Method of claim 22, wherein the pH of the aqueous solution is from 2.5 to 3.7.

28. Method of claim 22, wherein the pH of the aqueous solution is from 2.8 to 3.2.

29. Method of claim 22, wherein the effective concentration of n-acetylneuraminic acid (NANA) is delivered in from 2 to 8 administrations per day.

30. Method of claim 22, wherein the composition further comprises a thixotropic agent.

31. Method of claim 2, wherein the composition comprising n-acetylneuraminic acid (NANA) is administered orally.

32. Method of use of claim 31, wherein the composition comprising n-acetylneuraminic acid (NANA) comprises a daily dosage of from 20 to 200 grams n-acetylneuraminic acid (NANA).

33. Method of use of claim 31, wherein composition comprising n-acetylneuraminic acid (NANA) comprises a daily dosage of from 50 to 150 grams n-acetylneuraminic acid (NANA).

34. Method or use of any one of claim 31, wherein the composition comprising n-acetylneuraminic acid (NANA) is administered in from 1 to 20 doses.

35. Method or use of any one of claim 31, wherein the n-acetylneuraminic acid (NANA) is administered as an aqueous solution.

36. Method of claim 35, wherein the aqueous solution comprises an additional agent selected from the group consisting of a flavoring agent, a stabilization agent and a preservative agent, wherein the additional agent does not naturally occur with sialic acid.

37. The method of claim 2, wherein the subject is at risk for infection by SARS-CoV-2.

38. The method of claim 2, wherein the subject has COVID-19.

* * * * *